(12) United States Patent
Zoumalan

(10) Patent No.: US 10,496,949 B2
(45) Date of Patent: Dec. 3, 2019

(54) COMPOSITIONS AND METHODS FOR TREATING CUTANEOUS CONDITIONS

(71) Applicant: Christopher Zoumalan, Los Angeles, CA (US)

(72) Inventor: Christopher Zoumalan, Los Angeles, CA (US)

(*) Notice: Subject to any disclaimer, the term of this patent is extended or adjusted under 35 U.S.C. 154(b) by 0 days.

(21) Appl. No.: 15/806,300

(22) Filed: Nov. 7, 2017

(65) Prior Publication Data

US 2018/0185449 A1  Jul. 5, 2018

Related U.S. Application Data

(60) Provisional application No. 62/442,423, filed on Jan. 4, 2017.

(51) Int. Cl.
| | |
|---|---|
| A61K 47/32 | (2006.01) |
| A61P 17/10 | (2006.01) |
| A61P 17/00 | (2006.01) |
| A61P 17/02 | (2006.01) |
| A61K 9/00 | (2006.01) |
| A61K 31/375 | (2006.01) |
| A61K 36/23 | (2006.01) |
| A61K 36/886 | (2006.01) |
| A61K 38/18 | (2006.01) |
| A61K 38/20 | (2006.01) |
| A61K 47/10 | (2017.01) |
| A61K 47/34 | (2017.01) |
| A61K 47/36 | (2006.01) |
| A61K 9/06 | (2006.01) |
| G06Q 10/06 | (2012.01) |
| G07C 13/00 | (2006.01) |
| G06Q 10/10 | (2012.01) |
| G06K 9/00 | (2006.01) |
| G06K 9/62 | (2006.01) |
| G06K 9/66 | (2006.01) |
| G06N 20/00 | (2019.01) |
| G06Q 50/00 | (2012.01) |

(52) U.S. Cl.
CPC ...... *G06Q 10/06398* (2013.01); *A61K 9/0014* (2013.01); *A61K 9/06* (2013.01); *A61K 31/375* (2013.01); *A61K 36/23* (2013.01); *A61K 36/886* (2013.01); *A61K 38/1825* (2013.01); *A61K 38/1841* (2013.01); *A61K 38/2066* (2013.01); *A61K 47/10* (2013.01); *A61K 47/32* (2013.01); *A61K 47/34* (2013.01); *A61K 47/36* (2013.01); *A61P 17/00* (2018.01); *A61P 17/02* (2018.01); *A61P 17/10* (2018.01); *G06K 9/00369* (2013.01); *G06K 9/6202* (2013.01); *G06K 9/6268* (2013.01); *G06K 9/66* (2013.01); *G06N 20/00* (2019.01); *G06Q 10/1053* (2013.01); *G07C 13/00* (2013.01); *G06Q 50/01* (2013.01)

(58) Field of Classification Search
None
See application file for complete search history.

(56) References Cited

U.S. PATENT DOCUMENTS

| | | |
|---|---|---|
| 5,741,509 A | 4/1998 | Kushner |
| 7,241,451 B1 | 7/2007 | Edell et al. |
| 8,021,683 B2 | 9/2011 | Berlat |
| 8,263,114 B2 | 9/2012 | Berlat |
| 2008/0317822 A1 | 12/2008 | Azimi |
| 2009/0143333 A1 | 6/2009 | Palefsky et al. |
| 2010/0062085 A1 | 3/2010 | Widgerow |

OTHER PUBLICATIONS

Chang, B.S. and Hershenson, S. 2002. Practical approaches to protein formulation development in "Rationale Design of stable protein formulations-theory and practice" (J.F. Carpenter and M.C. Manning eds.) Kluwer Academic/ Plenum publishers, New York, 1-25) (Year: 2002).*

* cited by examiner

*Primary Examiner* — Vanessa L. Ford
*Assistant Examiner* — Sandra E Dillahunt
(74) *Attorney, Agent, or Firm* — Eandi Fitzpatrick LLP

(57) ABSTRACT

A composition for treating cutaneous condition is provided and has 0.200 wt. % *Aloe Barbadensis* Leaf Juice, 10.000 wt. % Cyclopentasiloxane and Dimethicone Crosspolymer, 6.000 wt. % Dimethicone, 2.000 wt. % Ethoxydiglycol, 2.000 wt. % Glycerin, Water and *Centella Asiatica* Extract Mixture, 18.000 wt. % Glycerin, 3.000 wt. % Hydroxyethyl Acetate/Sodium Acryloyldimethy Taurate Copolymer, 1.100 wt. % Phenoxyyethanol and Ethylexylglycerin, 2.00 wt. % PPG-12 SMDI Copolymer, 0.004 wt. % GMP Grade Recombinant Human TGF-B3, 0.075 wt. % GMP Grade Recombinant Human IL10, 0.250 wt. % GMP Grade Recombinant Human bFGF, 0.500 wt. % Sodium Hyaluronate, 2.000 wt. % Tetrahexyldecyl Ascorbate, and water to make 100%.

2 Claims, 10 Drawing Sheets

| Assessment Score | 0 | 1 | 2 | 3 | 4 | 5 |
|---|---|---|---|---|---|---|
| Vascularity | Normal | Pink | Red | Purple | - | - |
| Pigmentation | Normal | Hypopigmentation | Mixed | Hyperpigmentation (mild) | Hyperpigmentation (moderate) | Hyperpigmentation (Severe) |
| Pliability | Normal | Supple | Yielding | Firm | Ropes | Contracture |
| Height | Flat | <2mm | 2-5mm | >5mm | - | - |

FIG. 1

COMPOSITIONS AND METHODS FOR TREATING CUTANEOUS CONDITIONS

CROSS-REFERENCE TO RELATED APPLICATIONS

This application claims the benefit of U.S. Provisional Application No. 62/442,423, entitled Compositions And Methods For Treating Cutaneous And Mucosal Conditions, filed on Jan. 4, 2017.

FIELD OF THE INVENTION

The present composition relates generally to cutaneous and mucosal conditions and, more particularly, to a topically applied treatment composition and method to improve cutaneous conditions, such as scarring, acne, dermatitis, eczema, striae, burns and the like.

BACKGROUND OF THE INVENTION

Each year in the United States over 100 million patients acquire scars, some of which cause considerable medical and psychological problems. People with abnormal skin scarring may face physical, aesthetic, psychological and social consequences that may be associated with substantial emotional and financial costs.

Scars arise after almost every dermal injury—rare exceptions include tattoos, superficial scratches, and venepunctures. While some scars are considered medically trivial, they can be disfiguring, aesthetically unpleasant and cause severe itching, tenderness, pain, sleep disturbance, anxiety, depression and disruption of daily activities. Other psychosocial sequelae include development of post-traumatic stress reactions, loss of self-esteem and stigmatization, all leading to a diminished quality of life.

While there is considerable quantitative and qualitative variation in scarring potential between individuals, it is known that topical treatments can greatly reduce the appearance of scaring in a broad spectrum of scar types, ranging from fine line scars to a variety of abnormal scars, such as atrophic scars, scar contractures, hypertrophic scars and keloid scars.

While treatments may vary from non-invasive treatment, invasive treatment, to leave alone management, the most cost effective means when compared with results has traditionally been non-invasive treatments such as compression therapy, static and dynamic splints, acrylic casts, masks and clips, application of a variety of oils, lotions, and creams (e.g., "topicals"), the latter being the most widespread and having the most significant long term benefits.

These topicals do not just treat scars however, but are used to treat a wide range of dermatological conditions ranging from dermatitis, psoriasis, acne and the like.

Past therapies and topicals used to deal with scarring and conditions such as eczema and psoriasis have included the use of simple emollients. Topical steroids ranging from mild agents such as hydrocortisone (1%) through more potent materials such as clobetasol propionate (0.05%) have been used with the common inflammatory dermatoses. In addition, corticosteroids and immunosuppressents have been used to treat skin conditions. Vitamin D and its derivatives such as calcipotrial and tacolcitol and vitamin A and other retinoids have been used to treat dermatological problems. The vitamin D materials are used to treat acne.

For example, U.S. Pat. No. 7,241,451 to Edell describes a scar appearance reducing topical cream comprising: dimethicone copolyol, zinc PEG-30 dipolyhydroxystearate, vitamin D and onion extract.

Biocorneum is a scar cream that is composed solely of silicone cream and SPF 30 that has been shown to improve scars. A recent peer reviewed medical article showed that hyaluronic acid sponge with vitamin C improved the quality of scars. (A Clinical Evaluation of Efficacy and Safety of Hyaluronan Sponge with Vitamin C Versus Placebo for Scar Reduction. Amirlak B, Mahedia M, Shah N. Plast Reconstr Surg Glob Open. 2016 Jul. 11; 4(7):e792.) Studies have also been published in peer-reviewed medical journals.

Other vitamin treatment such as vitamin E have been used to decrease the collagen bonding during the wound healing process and to soften scars. Cutting vitamin E gelatin capsules in half and squeezing out the oil has been the most common way to apply vitamin E to wounds. However, vitamin E oil is messy and cutting the capsules in half is a tedious process. The addition of vitamins A and E in creams and lotions is also known, but such creams and lotions are often oily to the touch and do not dry so as to remain in an oily condition, or they take a long period of time to rub completely into the skin.

Furthermore, past therapies have also included silicone based wound dressings. For example, U.S. Pat. No. 5,741,509 to Berlat describes a wound dressing consisting of at least one non-volatile silicone fluid in admixture with fumed silica, one or more antibacterial active agent and at least one volatile diluent. U.S. Pat. No. 6,337,076 to Sudin describes a film-forming such as Collodion, which comprises a solution of pyroxilin (nitrocellulose) in a 25/75 mixture of alcohol and ether, or Flexible Collodion which comprises a mixture of Collodion with camphor and castor oil.

The above-described ad-hoc approaches have their respective limitations and unwanted side effects, however. The above-described emollients must be reapplied often, and the topical steroids found in some therapies have been linked to thinning skin, bruising, rashes and even Cushings Syndrome in extremely cases. Vitamin D materials may pass transdermally and can affect a user's systemic calcium metabolism.

It is clear that there is a need for a topical composition which can improve the condition of cutaneous injuries or conditions, striae, acne and burns, while avoiding the drawbacks of past and current therapies and compositions.

SUMMARY OF THE INVENTION

To achieve the forgoing and other aspects and in accordance with the purpose, a composition for treating cutaneous and/or mucosal conditions, striae and burns is presented.

The subject composition can be used to rejuvenate skin that has been damaged by scarring or that has simply been affected over the years by intrinsic aging, burns, striae and acne.

For the treatment of cutaneous injuries resulting in scarring, the composition is formulated to improve scars during the wound contraction phase though:
  providing enhanced hydration;
  antioxidant effects;
  allowing better reorganization of the collagen matrix;
  promoting wound contraction;
  softening and flattening scars;
  improving the discoloration of the scar;
  reducing the redness in the scar;

improving the discomfort associated with scars as they heal;

improving the appearance of acne, dermatitis, eczema; and treating burns.

The skin composition is non-irritating and can be used to soothe the pain of wounds and treatment of red, irritated, dry, cracked or itchy skin. It can also be used in treating atopic dermatitis, psoriasis and ichthyosis by moisturizing the skin. It can be generally used anywhere on the skin of a patient's body. For instance, it can also be applied to the patient's feet, chest, back, legs, ankles, arms, and/or wrists as desired.

The product or composition can also be applied to non-healing wounds such as diabetic wounds, pressure ulcers or injuries on various parts of the body including the head, neck, eyes, ears, torso and extremities.

This composition is based upon the discovery that these compositions, alone or in combination, improve the treatment and prevention of cutaneous injuries that result in scars.

In an embodiment of the present composition, a topical therapeutic composition for treating cutaneous or mucosal conditions, or both, is provided and comprises 0.001-1.000 wt. % Aloe Barbadensis Leaf Juice, 1.000-40.000 wt. % Cyclopentasiloxane and Dimethicone Crosspolymer, 0.50-15.000 wt. % Dimethicone, 1.00-10.000 wt. % Ethoxydiglycol, 0.100-5.000 wt. % Glycerin, Water and Centella Asiatica Extract Mixture, 1.000-30.000 wt. % Glycerin, 0.500-5.000 wt. % Hydroxyethyl Acetate/Sodium Acryloyldimethy Taurate Copolymer, 0.600-1.100 wt. % Phenoxyyethanol and Ethylexylglycerin, 1-6.00 wt. % PPG-12 SMDI Copolymer, 0.0010-0.1000 wt. % GMP Grade Recombinant Human TGF-B3, 0.010-0.3000 wt. % GMP Grade Recombinant Human IL10, 0.010-0.9000 wt. % GMP Grade Recombinant Human bFGF, 0.010-3.00 wt. % Sodium Hyaluronate, 0.1000-10.000 wt. % Tetrahexyldecyl Ascorbate, 30.000-80.000 wt % Water.

In an embodiment, a method of treating cutaneous injuries, conditions, or both, is provided which comprises topically applying to the site a composition of 0.001-1.000 wt. % Aloe Barbadensis Leaf Juice, 1.000-40.000 wt. % Cyclopentasiloxane and Dimethicone Crosspolymer, 0.50-15.000 wt. % Dimethicone, 1.00-10.000 wt. % Ethoxydiglycol, 0.100-5.000 wt. % Glycerin, Water and Centella Asiatica Extract Mixture, 1.000-30.000 wt. % Glycerin, 0.500-5.000 wt. % Hydroxyethyl Acetate/Sodium Acryloyldimethy Taurate Copolymer, 0.600-1.100 wt. % Phenoxyyethanol and Ethylexylglycerin, 1-6.00 wt. % PPG-12SMDI Copolymer, 0.00100-0.1000 wt. % GMP Grade Recombinant Human TGF-B3, 0.010-3000 wt. % GMP Grade Recombinant Human IL10, 0.010-0.9000 wt. % GMP Grade Recombinant Human bFGF, 0.010-2.00 wt. % Sodium Hyaluronate, 0.1000-10.000 wt. % Tetrahexyldecyl Ascorbate, 30.0000-80.000 wt % Water.

Other features, advantages and aspects of the present composition will become more apparent and be more readily understood from the following detailed description, which should be read in conjunction with the accompanying drawings.

BRIEF DESCRIPTION OF THE DRAWINGS

Other features, advantages and aspects of the present composition will become more apparent and be more readily understood from the following detailed description, which should be read in conjunction with the accompanying drawings in which:

FIG. 1 is a table showing a modified Vancouver Scar Scale showing the effects of treatment using the composition in an embodiment of the present composition;

DETAILED DESCRIPTION OF THE PREFERRED EMBODIMENTS

Figure 2:
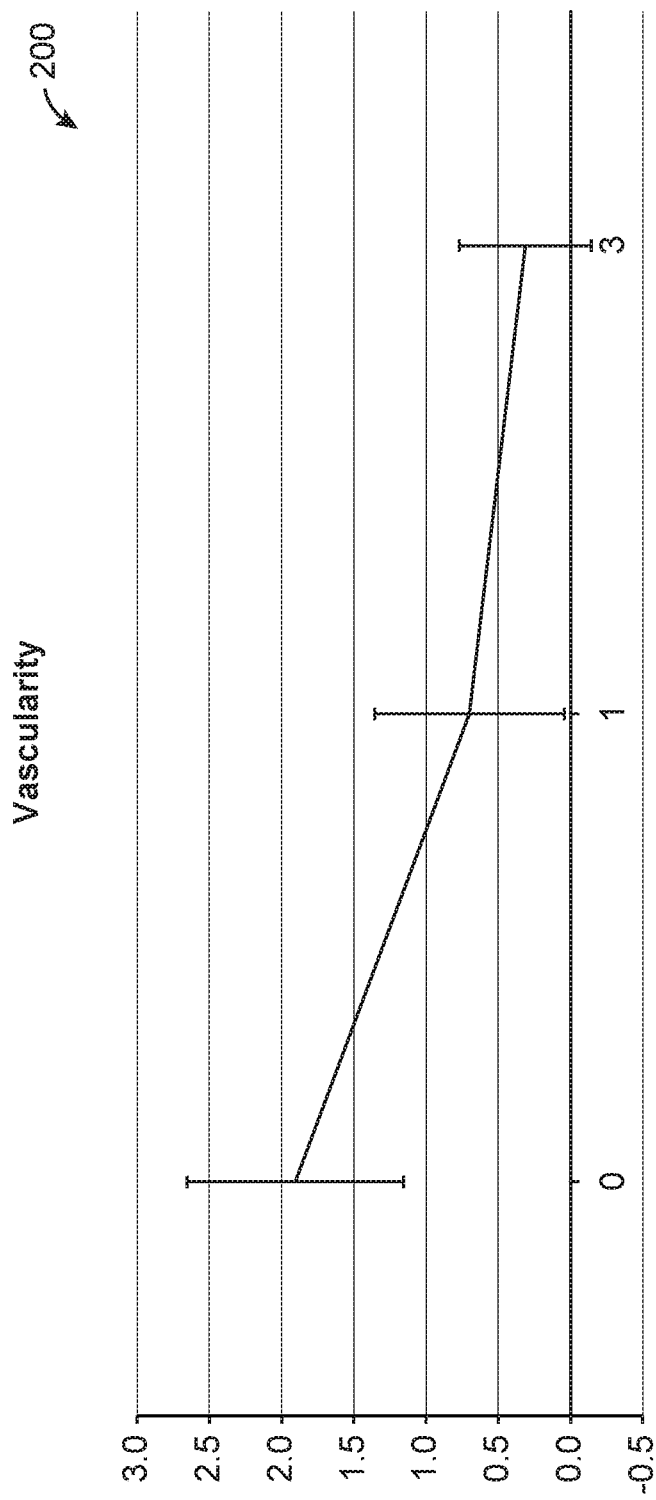
FIG. 2 is a graph showing the improvement in the vascularity of the scar in those patients using the composition in an embodiment of the present composition.

The present composition is best understood by reference to the detailed description and examples set forth herein.

Embodiments of the composition are discussed below with reference to the examples. However, those skilled in the art will readily appreciate that the detailed description given herein with respect to these examples is for explanatory purposes as the composition extends beyond these limited embodiments. For example, it should be appreciated that those skilled in the art will, in light of the teachings of the present composition, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the composition that are too numerous to be listed but that all fit within the scope of the composition. Also, singular words should be read as plural and vice versa and masculine as feminine and vice versa, where appropriate, and alternative embodiments do not necessarily imply that the two are mutually exclusive It is to be further understood that the present composition is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present composition. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Unless defined otherwise, all technical and scientific terms used herein have the same meanings as commonly understood by one of ordinary skill in the art to which this composition belongs. Preferred methods, techniques, devices and materials are described, although any methods, techniques, devices, or materials similar or equivalent to those described herein may be used in the practice or testing of the present composition.

Definitions

"*Aloe Barbadensis*" refers to an extract of the species that has *A. barbadensis* Mill., *Aloe indica* Royle, *Aloe perfoliata* L, *A. vulgaris* Lam and the like.

"*Centella asiatica*" is defined as centella and gotu kola, a herbaceous, frost-tender perennial plant of the family Mackinlayaceae or subfamily Mackinlayoideae of family Apiaceae.

"Composition" references to that specific composition contemplated in the Summary of the Invention that can be used to rejuvenate skin that has been damaged by scarring or which has simply been affected over the years by intrinsic aging, burns and scarring.

"Cyclopentasiloxane and Dimethicone Crosspolymer" is defined as a mixture of high molecular weight silicone elastomers (dimethicone crosspolymer) in cyclopentasiloxane.

"Derivatives" as used herein refers to structurally similar compounds that exhibit a common activity (e.g., antioxidant) and contain at least one significant, common structural element with the compound from which it is derived, which common structural element provides the common activity.

"Dimethicone" also known as "polymethylsiloxane" is a silicon-based polymer used as a lubricant and conditioning agent.

"Ethoxydiglycol" also known as Diethylene Glycol Monoethyl Ether is a cosmetic grade solvent that conforms to the current USP/NF monographs.

"Glycerin, Water and *Centella Asiatica* Extract Mixture" refers to a mixture of glycerin, water and a herbaceous, frost-tender perennial plant in the flowering plant family Apiaceae, subfamily Mackinlayoideae.

"Glycerin" as used herein refers to Glycerol as is generally obtained from plant and animal sources where it occurs as triglycerides.

"Growth factors" as used herein refers to plant growth factors such as kinetin, a plant-based growth factor that functions mainly to protect the skin from free radical damage. "Growth factors" may also refer to human or synthetic growth factors. Synthetic growth factors may be developed to be approximately identical to growth factors found in human skin, designed to enhance epidermal growth and keratinization, and may comprise, for example, transforming growth factor (TGF) Beta 1, 2, 3, Interleukin-10 (IL-10) and basic Fibroblast growth factor (bFGF).

"Hydroxyethyl Acetate/Sodium Acryloyldimethyl Taurate Copolymer", is a polymer is a pre-neutralized powder, dispersible in the oil or water phase in cold or hot process formulations. It is able to emulsify and stabilize formulations with up to 50% oil phase.

"Pharmaceutically-acceptable topical carrier" and equivalent terms refer to an inactive liquid or cream vehicle capable of suspending or dissolving the aromatic aldehyde and having the properties of being nontoxic and non-inflammatory when applied to the skin. Representative carriers include water, oils, both vegetable and mineral, cream bases, lotion bases, ointment bases and the like. These bases include suspending agents, thickeners, penetration enhancers and the like. Their formulation is well known to those in the art of cosmetics and topical pharmaceuticals.

"Phenoxyyethanol and Ethylexylglycerin" refers to a glycerin-based polyol compound derived from sugar alcohol.

"Scar tissue" is used to refer to the connective tissue that forms a scar and which consists primarily of fibroblasts in new scars and collagen fibers in older scars. Scar tissue is generally characterized by red discoloration, edema, irritation and dehiscence. Patients afflicted with scar tissue typically have visible indications of past wounds located on their skin.

"Silicone cream" (i.e., Dimethicone 10%) is defined as a cream or gel having polymers that include any inert, synthetic compound made up of repeating units of siloxane, which is a chain of alternating silicon atoms and oxygen atoms, frequently combined with carbon and/or hydrogen.

"Sodium Hyaluronate" refers to sodium salt of hyaluronic acid. It is a glycosaminoglycan and long-chain polymer of disaccharide units of Na-glucuronate-N-acetylglucosamine.

"Tetrahexyldecyl Ascorbate" is an oil-soluble vitamin C ester which has anti-oxidant activity, inhibiting lipid peroxidation.

"Therapeutically effective dose" is defined as a dose of a composition of this composition which, when applied topically to the skin of a patient afflicted with a dermatologic or other cosmetic or medical condition, or when administered by another route, results in an observable improvement in the patient's condition.

"Topical" refers to a mode of administration and means that a material is administered by being applied to the skin.

"Topically effective" means that a material, when applied to the skin, produces a desired pharmacological result either locally at the place of application or systemically as a result of transdermal passage of an active ingredient in the material.

Now, with reference to the composition for improving the appearance of skin, and in particular, scars, the composition of the present composition is, in some embodiments, applied topically, and may be a cream, gel, ointment, lotion, paste, jelly or other topical.

When applied topically, the composition of the present composition reduces the appearance of scars by helping them to fade and diminish, consequently becoming less noticeable. The topically applied composition of the present composition helps raised and discolored scars become flatter, softer, smoother and closer to the skin's natural tone. In some embodiments of the present composition, it may be applied multiple times a day to encourage breaking up collagen or scar tissue, reducing the appearance of the scar tissue. It may also be used to treat acne, burns and reduces striae.

The composition of the present composition may comprise a base of water and glycerin, and may further comprise GMP Grade Recombinant Human bFGF, GMP Grade Recombinant Human TGF-B3, GMP Grade Recombinant Human IL10 and a Cyclopentasiloxane/Dimethicone Crosspolymer mixture.

The cream, ointment or gel of the present composition may be an oil silicone and water emulsion containing a mixture of protective oils, silicones and waxes. Optionally, a mixture of vitamins, such as vitamins C, E and K, as well as an onion extract, may be included in the cream, gel, ointment, capsule or drop of the present composition.

The glycerin acts as a protective barrier to the skin that reduces trans-epidermal water loss that helps to increase collagenase activity. This results in the reduction of collagen formation and reduces the appearance of scars. The glycerin and water also provides an environment facilitating the skin's natural healing and reparative properties that work to reduce the appearance of scars over time.

In embodiments of the present composition, growth factors are employed which may be derived from synthetic, plant, animal and human sources. These provide a nourishment for the skin during the healing process.

In other embodiments, the growth factors may comprise transforming growth factor (TGF) Beta 3, Interleukin-10 (IL-10) and basic fibroblast growth factor (bFGF). The growth factors function to alleviate a myriad of dermal issues and accelerate wound healing. In some embodiments, recombinant growth factors may be used, while in others, those derived from human stem cells may be used. In optional embodiments, the composition may further comprise anti-TGF Beta 1 antibody and/or anti-TGF Beta 2 antibody function to control controls proliferation, differentiation and other functions in many cell types. Many cells synthesize TGF B1 and have specific receptors for it, and negatively regulates growth factors. In optional embodiments, they play important role in tissue remodeling thus reducing the appearance of scarring.

The composition may further comprise interleukin-10, which is capable of inhibiting synthesis of pro-inflammatory cytokines such as IFN-$\gamma$, IL-2, IL-3, TNF$\alpha$ and GM-CSF made by cells such as macrophages and Th1 T cells, while also displaying an ability to suppress the antigen-presentation capacity of antigen presenting cells. In this way, the appearance of scar tissue is diminished. During both wound healing of normal tissues and tumor development, the action of heparan sulfate-degrading enzymes activates bFGF, thus mediating the formation of new blood vessels and minimizing scar appearance.

The vitamins and plant extracts listed in Table 1 are known to comprise antioxidant properties and play a role in collagen synthesis while also helping prevent and treat ultraviolet (UV)-induced photodamage. These vitamins are known to be vital to proper skin nutrition. Also, the active ingredients may include liposomes to ensure the vitamins are delivered to the proper skin depth.

As shown in Table 1, the base consists of oils, waters and water-soluble components. In the preferred embodiment, the base is an emulsion of oils, water and water-soluble components. Generally, the base may include any emollients, lubricants, emulsifying agents, thickening agents, humectants, preservatives, antifungal agents, fragrances and wetting agents known in the art to be suitable for use in a moisturizing skin cream base. Also, any mixing methods known in the art to be suitable for mixing an oil and water emulsion for the purposes of forming a moisturizing skin cream may be used to mix the base ingredients.

The scar diminishing composition should contain a therapeutically effective amount of each of the above described ingredients, and also those described in Table 1. The ingredients of the therapeutic composition of the present composition are summarized in Table 1 below with respect to a description thereof, the active ingredients therein, percentages by weight range for each active ingredient, and the benefits thereof.

TABLE 1

| Ingredient | Minimum Range % | Current % | Maximum Range % | Description | Trade Name | Benefits |
| --- | --- | --- | --- | --- | --- | --- |
| Aloe Barbadensis Leaf Juice | 0.001 | 0.200 | 1.000 | An extract of the species has A. barbadensis Mill., Aloe indica Royle, Aloe perfoliata L, A. vulgaris Lam and the like. | Terra Aloe Vera 200× | Aloe-derived ingredients enhance the appearance of dry or damaged skin by reducing flaking and restoring suppleness |
| Cyclopentasiloxane and Dimethicone Crosspolymer | 1.000 | 10.000 | 40.000 | A mixture of high molecular weight silicone elastomers (dimethicone crosspolymer) in cyclopentasiloxane | Dow Corning ® 9045 | Facilitate moisturization and emolliency for smoother, softer skin, and offer pleasing sensory benefits that include reduced tackiness, barrier protection, and moisturization |

TABLE 1-continued

| Ingredient | Minimum Range % | Current % | Maximum Range % | Description | Trade Name | Benefits |
|---|---|---|---|---|---|---|
| Dimethicone | 0.50 | 6.000 | 15.000 | Also called polymethylsiloxane it is a silicon-based polymer used as a lubricant and conditioning agent. | Dimethisil 350 | to help restore and revitalize skin Functions as antifoaming agent, skin-conditioning agent—occlusive; skin protectant; |
| Ethoxydiglycol | 1.000 | 2.000 | 10.000 | Also known as Diethylene Glycol Monoethyl Ether, is a cosmetic grade solvent that conforms to the current USP/NF monographs. | | Useful and appropriate for skin care preparations where it acts as a solvent and carrier |
| Glycerin, Water and Centella Asiatica Extract Mixture | 0.100 | 2.000 | 5.000 | Herbaceous, frost-tender perennial plant in the flowering plant family Apiaceae, subfamily Mackinlayoideae. | Gotu Kola GL 50 | Functions to reduce swelling and improve blood flow, prevent scarring and wound healing |
| Glycerin | 1.000 | 18.000 | 30.000 | Glycerol is generally obtained from plant and animal sources where it occurs as triglycerides. | Glycerol 99.7% | — |
| Hydroxyethyl Acetate/Sodium Acryloyldimethy Taurate Copolymer | 0.500 | 3.000 | 5.000 | A polymer is a pre-neutralized powder, dispersible in the oil or water phase in cold or hot process formulations. It is able to emulsify and stabilize formulations with up to 50% oil phase. | Sepinov EMT | Functions as a stabilizing properties at a low level and in presence of a high percentage oily phase. It produces translucent formulas without electrolytes. |
| Phenoxyyethanol and Ethylexylglycerin | 0.600 | 1.100 | 1.100 | Glycerin based polyol compound derived from sugar alcohol. | AE Protek Plus | The addition of ethylhexylglycerin affects the interfacial tension at the cell membrane of microorganisms, improving the preservative activity of phenoxyethanol. |

TABLE 1-continued

| Ingredient | Minimum Range % | Current % | Maximum Range % | Description | Trade Name | Benefits |
|---|---|---|---|---|---|---|
| PPG-12 SMDI Copolyper | 1 | 2.000 | 6.000 | Copolymer of saturated methylene diphenyldiisocyanate and PPG-12 monomers. | Polyprepolymer | Functions as an anti-irritant and stabilizer |
| GMP Grade Recombinant Human TGF-B3, | 0.0010 | 0.004 | 0.1000 | A type of protein, known as a cytokine, which is involved in cell differentiation, embryogenesis and development. | TGF B3 | Alleviates a myriad of dermal issues and accelerate wound healing. |
| GMP Grade Recombinant Human IL10 | 0.010 | 0.075 | 0.3000 | An anti-inflammatory cytokine. In humans, interleukin 10 is encoded by the IL10 gene | IL-10 | Inhibits synthesis of pro-inflammatory cytokines such as IFN-γ, IL-2, IL-3, TNFα and GM-CSF made by cells such as macrophages and Th1 T cells, while also displaying an ability to suppress the antigen-presentation capacity of antigen presenting cells |
| GMP Grade Recombinant Human bFGF | 0.010 | 0.250 | 0.9000 | Present in basement membranes and in the subendothelial extracellular matrix of blood vessels. | bFGF | Alleviates a myriad of dermal issues and accelerate wound healing. |
| Sodium Hyaluronate | 0.010 | 0.500 | 2.000 | Sodium salt of hyaluronic acid. It is a glycosaminoglycan and long-chain polymer of disaccharide units of Na-glucuronate-N-acetylglucosamine. | Dermatein | Facilitate the absorption of biomacromolecules and function as a nanocarrier. In barrier-deficient skin it restricted the delivery of biomacromolecules to the stratum corneum and viable epidermis. |
| Tetrahexyldecyl Ascorbate | 0.1000 | 2.000 | 10.000 | Oil-soluble Vitamin C ester which has anti-oxidant activity, inhibiting lipid peroxidation. | BV-OSC | Mitigates the damaging effects of UV exposure, stimulate collagen production as well as clarifying and brightening the skin by inhibiting melanogenesis (the production of |

TABLE 1-continued

| Ingredient | Minimum Range % | Current % | Maximum Range % | Description | Trade Name | Benefits |
|---|---|---|---|---|---|---|
| | | | | | | pigment) thereby promoting a more even skin tone |
| Water | 30.000 | 52.871 | 80.000 | — | — | — |

EXAMPLE 1

Composition 1

A therapeutic composition is prepared as described above using the following proportions of ingredients: 0.200 wt. % *Aloe Barbadensis* Leaf Juice, 10.000 wt. % Cyclopentasiloxane and Dimethicone Crosspolymer, 6.000 wt. % Dimethicone, 2.000 wt. % Ethoxydiglycol, Ethoxydiglycol, 2.000 wt. % Glycerin, Water and *Centella Asiatica* Extract Mixture, 18.000 wt. % Glycerin, 3.000 wt. % Hydroxyethyl Acetate/Sodium Acryloyldimethy Taurate Copolymer, 1.100 wt. % Phenoxyyethanol and Ethylexylglycerin, 2.000 wt. % PPG-12 SMDI Copolymer, 0.004 wt. % TGF B3, 0.075 IL-10, 0.250 wt. % bFGF, 0.500 wt. % Sodium Hyaluronate, 2.000 Tetrahexyldecyl Ascorbate, 52.871 wt. % water.

EXAMPLE 2

Evaluation of Test Subjects

A controlled clinical study was performed on the Composition listed in Table 1, by prospectively evaluating its effects on scars through one arm of the study (Study Arm 1) and also through a comparison study by directly comparing the Composition to regular silicone cream (Study Arm 2). In our study, the Composition and the silicone cream had similar texture, color and fragrance. In both study arms, the creams were applied twice daily, once in the morning and once in the evening.

The study shows a significant improvement in the appearance of the scars. There was an overall improvement in the appearance of the scar by 46.1% at one month and up to 73.4% by month 3 when averaging all four Vancouver scar scale variables of vascularity, pigmentation, pliability and height of the scar.

The study also shows that the Composition is superior to regular silicone cream, in all parameters of appearance and patient subject assessment over a 3-month follow-up. More specifically, when comparing the two creams, a 22.0% improvement was noted in vascularity, a 39.0% improvement in pigmentation, a 44.3% improvement in pliability and a 31.7% improvement in the pigmentation in the scars that used the Composition in comparison to silicone cream, $p<0.05$.

An evaluation of the safety and efficacy of the Composition using patients that had a scar less than 1-year-old was performed. Adults over the age of 18 with prior incisions from surgery (elective or trauma) on their face, trunk or upper extremities were included. Adults were required to speak English, if not, they required a translator. The patients did not receive other treatments before participating in the study. The study was approved by an Institutional Review Board, and consent forms, which conformed to the ethical guidelines of the 1975 Declaration of Helsinki, were accepted and signed by each patient. Inclusion criteria were wounds at least two weeks status post repair and up to one year. Pregnant women were excluded from the study. Wounds that required further treatment such as an intralesional steroid injection were excluded from the study.

Study Arm 1 was a prospective clinical study evaluating the efficacy of the scar cream, which we refer to as the Composition. The participants were provided the Composition starting at least two weeks after the incisions were created. Scars that were older than 1 year were excluded from the study. The cream was applied twice daily. Study Arm 2 s an investigator-blinded, randomized, multi-center comparison study comparing the Composition to regular silicone cream. The participants are assigned both silicone cream and the Composition starting at least two weeks after the incisions were created. Scars that were older than 1 year were excluded from the study. Both scar creams were packaged in similar bottles. Each product was randomly assigned to treat half the designated scar area twice daily. In cases of bilateral scars, such as in upper lid eyelid surgery or bilateral facial incisions which are nearly symmetric in size, the creams were randomly assigned to each treat one of the sides twice daily. In cases where one scar was being treated by both creams, the scar was designated as right side vs left side (or top vs bottom) to designate which side is being treated by the silicone cream or the Composition.

Clinical Efficacy

Referring now to FIG. 1, a modified Vancouver Scar Scale is presented at 100. For both arms included in the study, the investigator evaluated the scar at each visit using the modified Vancouver Scar Scale 100.

Still referring to FIG. 1, the initial column on the left lists the different characteristics of the scar (e.g., vascularity, pigmentation, pliability and height) while the top row provides the different assessment scores (e.g., 0-5). The applicable rating scale for each of the potential scar characteristics are as follows:

Vascularization: 0=normal, 3=severe
Pigmentation: 0=normal 3=severe
Pliability: (width) 0=normal, 5=severe
Height: 0-normal, 3=severe
Participant Self-assessment Participants evaluated their assessment and tolerability of the scar cream(s) using a 4-point scale at each visit. The self-assessment scores are further discussed in relation to FIG. 10. The scale for this self-assessment is as follows:

Overall appearance: 0=no change, 3=significant improvement
Texture: 0=no change, 3=significant improvement
Softness: 0=no change, 3=significant improvement
Tolerability: 0=no issues, 3=severe intolerability
Participant Photography Participants were photographed at each visit using standardized digital photography in the same room using the same lighting conditions and camera settings.

Statistical Analysis

Clinical grading scores at each visit (start of study, week 4 and week 12) will be compared with their corresponding baseline score using a paired Students t-test. In this analysis, identified differences with P-values less than 0.05 will be considered statistically significant.

Results

Study Arm 1: Prospective Study Evaluating the Composition

In the first segment of the study, 22 patients that had 33 scars were included in the study; 20 were female and 2 were male, average age 48+/−12 years. The patients were followed for 3 months. The mean start of application of scar cream was 8.6 weeks post surgery (+/−9.15 weeks). There was a statistically significant improvement in all four clinical parameters (vascularity, pigmentation, pliability, heights) in the Vancouver scar scale at the start of the study, 1, and 3 month intervals for those applying the composition over their scars (See Tables 2-4). During the follow-up period, the participants self-reported statistically significant improvements in the overall appearance, texture, and softness of the scar using the composition during the 3-month follow-up. There were no issues of tolerability to the scar cream except for some minor irritation in 2 patients when they initially applied the cream, which self-resolved after one week of continued application.

Referring now to FIG. 2, a graph showing the improvements in the vascularity of the scar in those patients using the Composition throughout the study is shown at 200. This graph shows the improvements over a 3-month period of time in which the cream was used by the patients. Located along the X-axis of this graph is the month in which the reading was taken (e.g., 0=start of study, 1=$1^{st}$ month after beginning usage, 3=$3^{rd}$ month after beginning usage). Located along the Y-axis of this graph is the vascularity reading at the month denoted in the X-axis. In this particular graph, the P value is less than 0.05.

Figure 3:
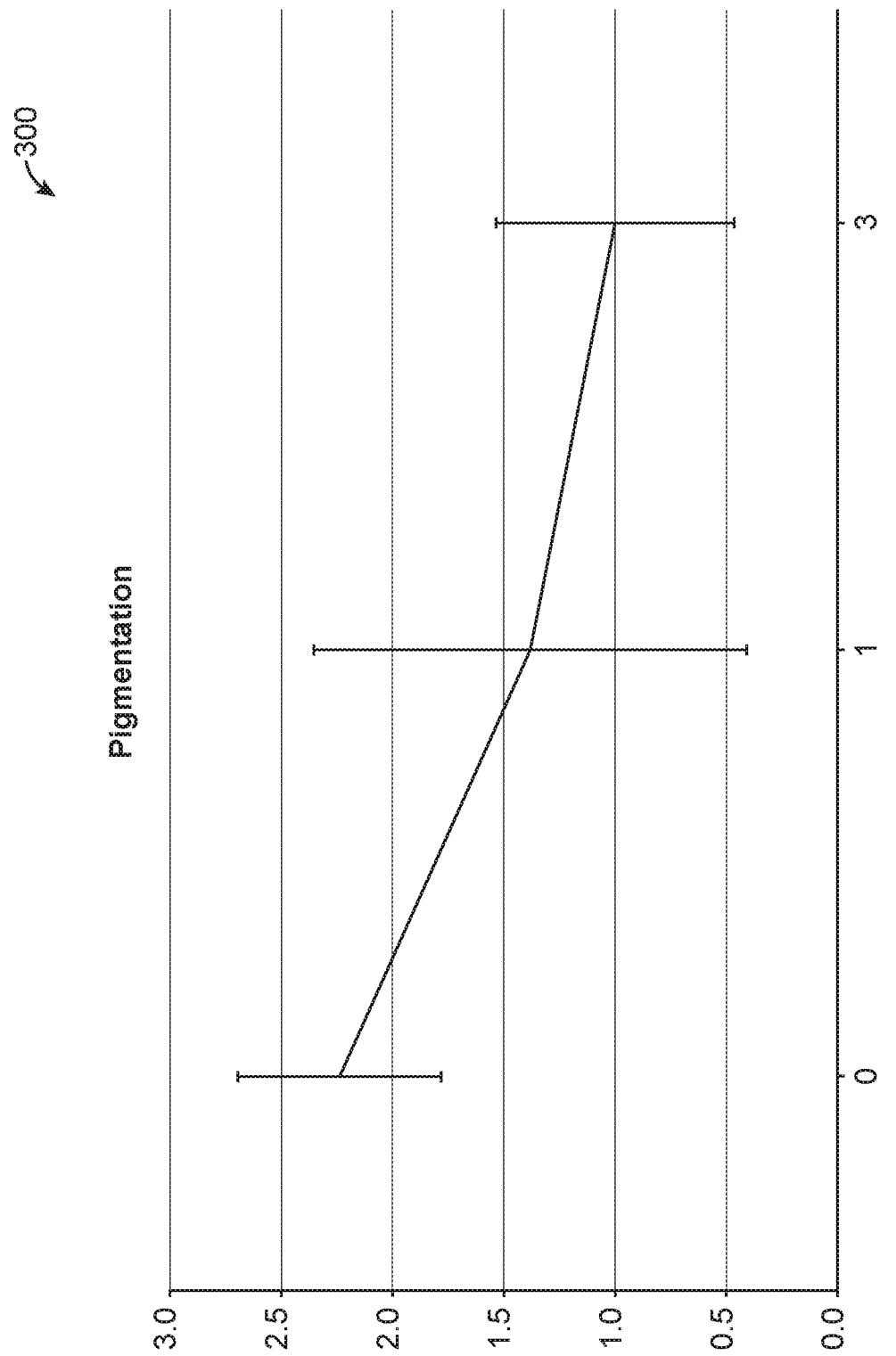
FIG. 3 is a graph showing the improvement in the pigmentation of the scar in those patients using the composition in an embodiment of the present composition.

Referring now to FIG. 3, a graph showing the improvements in pigmentation of the scar in those patients using the Composition over the course of the study is shown at 300. This graph shows the improvements over a 3-month period of time in which the cream was used by the patients. Located along the X-axis of this graph is the month in which the reading was taken (e.g., 0=start of study, 1=$1^{st}$ month after beginning usage, 3=$3^{rd}$ month after beginning usage). Located along the Y-axis of this graph is the amount of pigmentation present at the month denoted in the X-axis. In this particular graph, the P value is less than 0.05.

Figure 4:
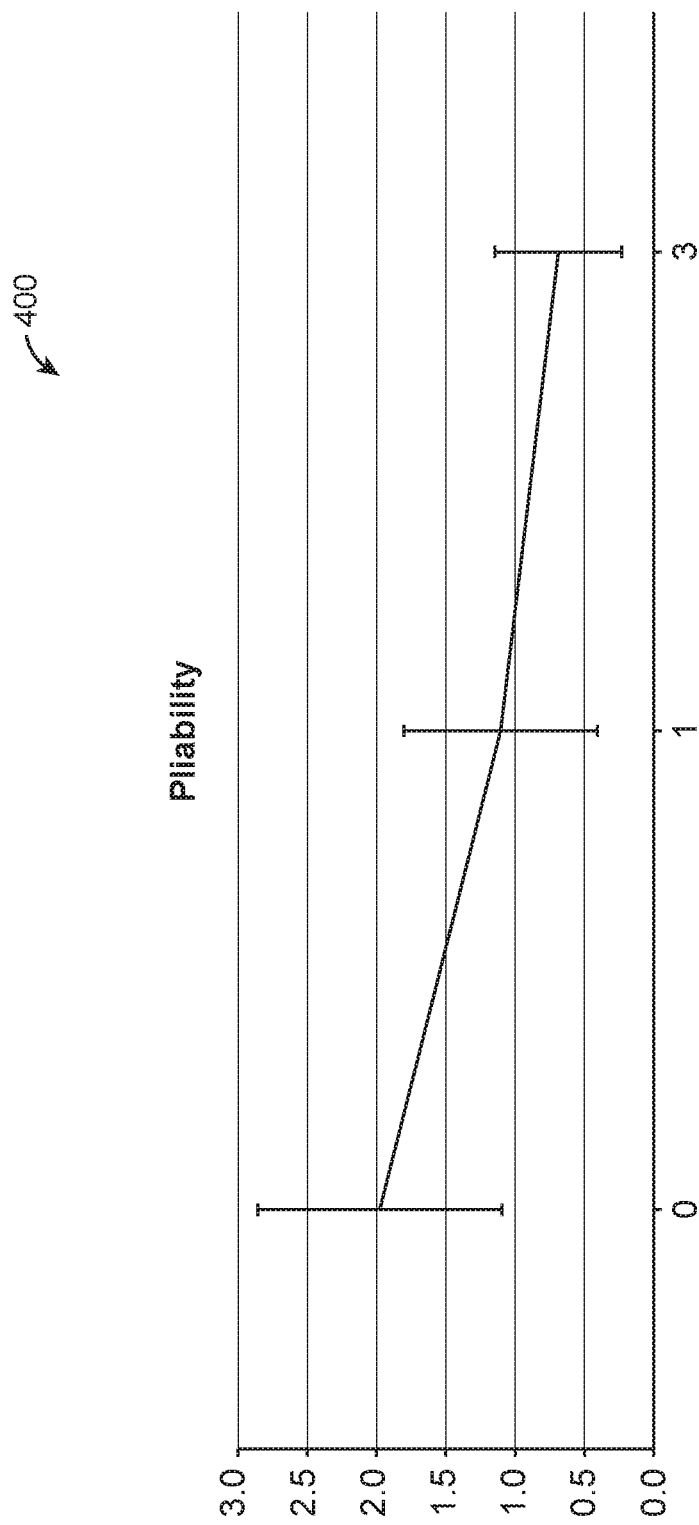
FIG. 4 is a graph showing the improvement in the pliability of the scar in those patients using the composition in an embodiment of the present composition.

Referring now to FIG. 4, a graph showing the improvements in pliability of the scar in those patients using the Composition over the course of the study is shown at 400. This graph shows the improvements over a 3-month period of time in which the cream was used by the patients. Located along the X-axis of this graph is the month in which the reading was taken (e.g., 0=start of study, 1=$1^{st}$ month after beginning usage, 3=$3^{rd}$ month after beginning usage). Located along the Y-axis of this graph is the pliability level at the month denoted in the X-axis. In this particular graph, the P value is less than 0.05.

Figure 5:
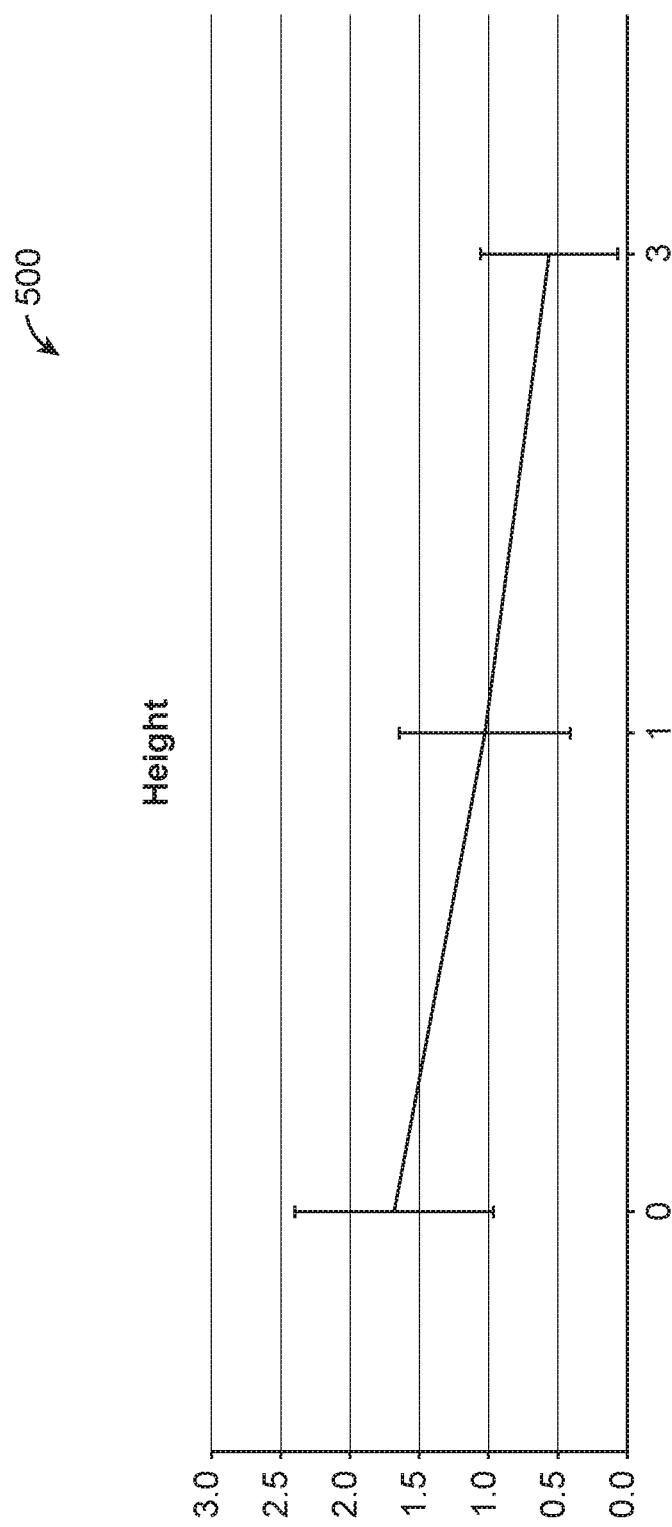
FIG. 5 is a graph showing the improvement in the height of the scar in those patients using the composition in an embodiment of the present composition.

Referring now to FIG. 5, a graph showing the improvements in the height of the scar in those patients using the Composition over the course of the study is shown at 500. This graph shows the improvements over a 3-month period of time in which the cream was used by the patients. Located along the X-axis of this table is the month in which the reading was taken (e.g., 0=start of study, 1=$1^{st}$ month after beginning usage, 3=$3^{rd}$ month after beginning usage). Located along the Y-axis of this graph is the height of the scar at the month denoted in the X-axis. In this particular graph, the P value is less than 0.05.

With references to FIGS. 1-5, there was an overall improvement in the appearance of the scar by 46.1% at one month and up to 73.4% by month 3 when averaging all four Vancouver scar scale variables of vascularity, pigmentation, pliability, and height of the scar. More specifically, the following improvements were noted in the appearance of the scar: (i) 63.1% improvement by month 1 and up to an 86.3% improvement by month 3 in the vascularity of the scar; (ii) up to a 38.1% improvement by month 1 and up to a 55.1% improvement by month 3 in the pigmentation of the scar; (iii) up to a 44.1% improvement by month 1 and up to an 85.3% improvement by month 3 in the pliability of the scar; and (iv) up to a 39.2% improvement by month 1, and up to an 66.6% improvement by month 3 in the height of the scar.

Study Arm 2: Head-to-Head Comparison of the Composition to Silicone Cream

In the second arm of the study, 29 patients that had 43 scars were included in the double-blinded study for analysis. 25 were female and 4 were male with an average age of 49 years. A two-tailed paired t-test was used for statistical analysis. The patients were followed for 3 months. One patient was excluded from the study due to headaches of uncertain etiology after beginning the study. The headaches resolved after 2 weeks of cessation from both creams. Five patients self-excluded themselves from the study at month 1 and 2 self-excluded themselves from the study at month 3 (a total of 7 patients), noticing a clinically significant difference between the two creams such that the Composition was selected by all 7 patients as being superior in results in comparison to silicone cream. Although the patients were blinded to the creams, all 7 identified the scar that was treated by the Composition as the far superior one and elected to be excluded from the study.

The mean start for application of the scar cream was 8.7 weeks post-surgery (+/−5.9 weeks). In the repeated measure analysis, all parameters of the modified Vancouver scar scale improved in both the Composition and silicone cream groups. However, when comparing the two creams, all parameters of the Vancouver scar scale were better in the Composition group when compared to the silicone cream group. More specifically, there was a statistically significant improvement in all 4 parameters evaluated—vascularity, pigmentation, pliability and height—in the scars treated by the Composition when compared to the silicone cream at months 1 and 3, all of which is further discussed with reference to FIGS. 6-9. There were no issues of tolerability to either scar creams except for some minor irritation in 3 patients when they initially applied the creams, which self-resolved after one week of continued application.

More specifically, when comparing the two creams, a 22.0% improvement was noted in vascularity, a 39.0% improvement in pigmentation, a 44.3% improvement in pliability and a 31.7% improvement in height in the scars that used the Composition in comparison to silicone cream, with a $p<0.05$.

Figure 6:
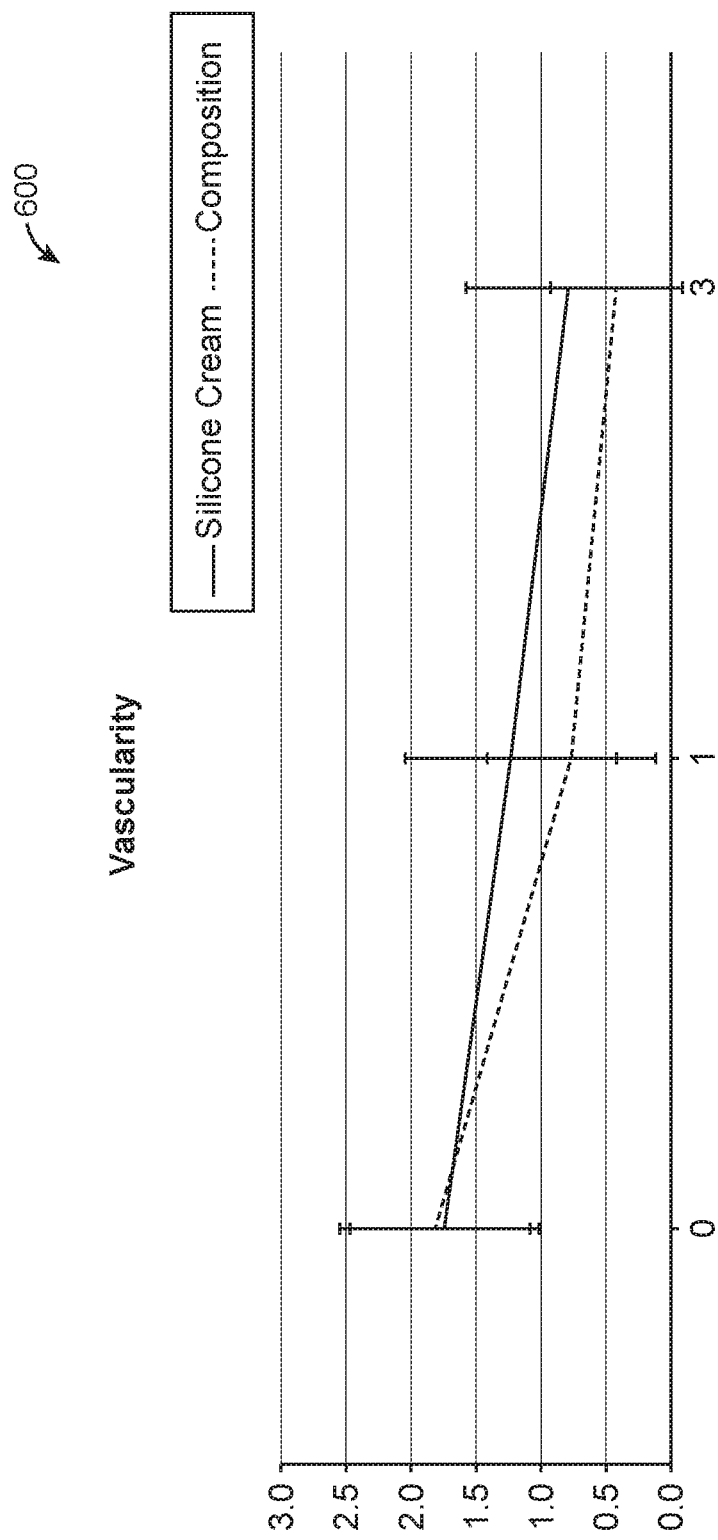
FIG. 6 is a graph showing the improvement in the vascularity of the scar in those patients using the composition in an embodiment of the present composition.

Referring now to FIG. 6, a graph showing the improvements in vascularity of the scar over the course of the study for each of the creams tested is shown at 600. The dashed line shows the results for the Composition, whereas the solid line shows the results for the silicone cream for each of FIGS. 6-9. Located along the X-axis of this graph is the month in which the reading was taken (e.g., 0=start of study, 1=$1^{st}$ month after beginning usage, 3=$3^{rd}$ month after beginning usage). Located along the Y-axis of this graph is the amount of vascularization in the scar at the month denoted in the X-axis. In this particular table, the P value is less than 0.05. Overall, this graph shows that the improvements in vascularity of the scar for those patients who used the Composition greatly increased over the 3-month period as compared to those patients who used the silicone cream.

Figure 7:
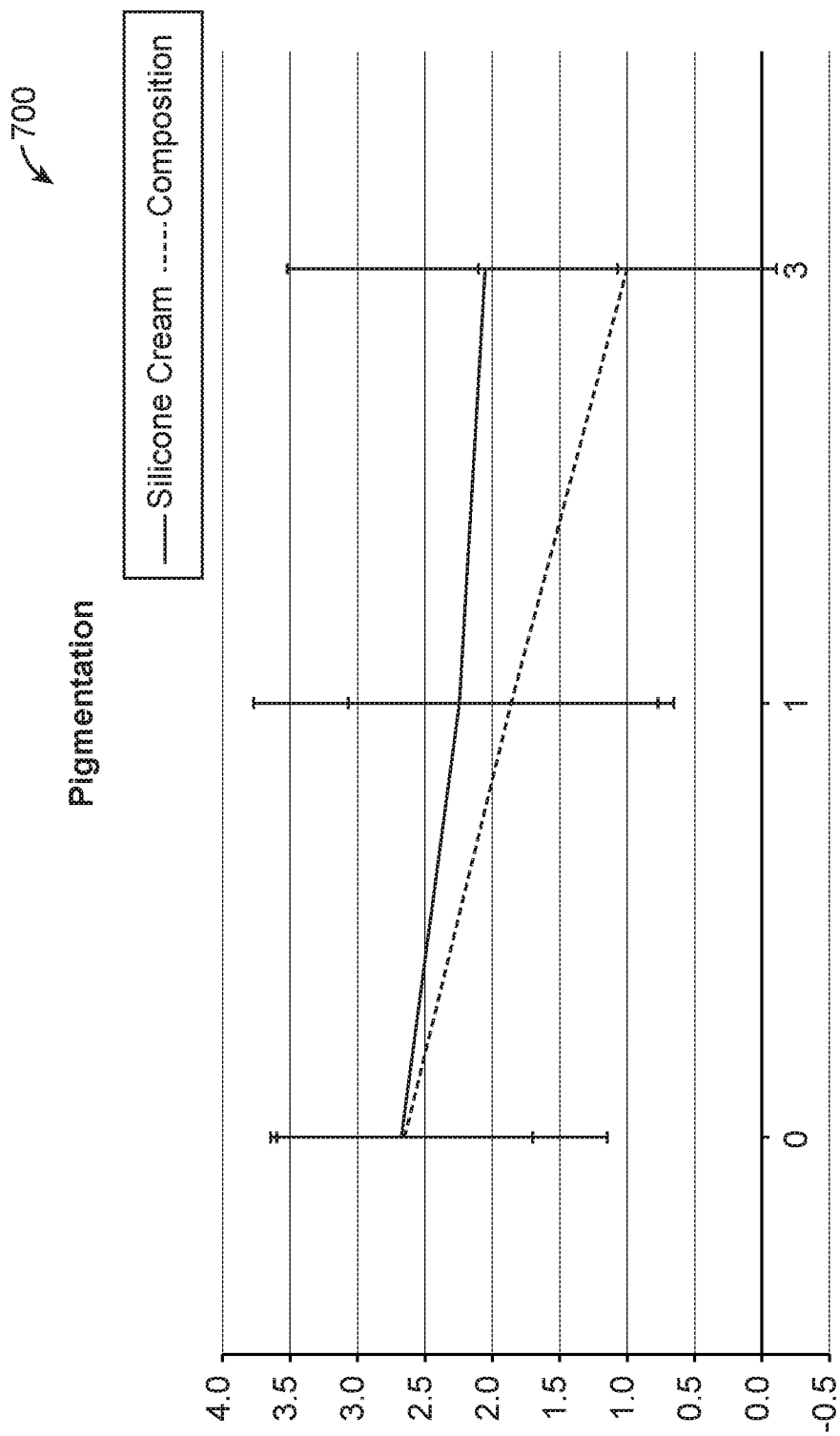
FIG. 7 is a graph showing the improvement in the pigmentation of the scar in those patients using the composition in an embodiment of the present composition.

Referring now to FIG. 7, a graph showing the improvements in pigmentation of the scar over the course of the study for each of the creams tested is shown at 700. The dashed line shows the results for the Composition, whereas the solid line shows the results for the silicone cream. Located along the X-axis of this graph is the month in which the reading was taken (e.g., 0=start of study, 1=$1^{st}$ month after beginning usage, 3=$3^{rd}$ month after beginning usage). Located along the Y-axis of this graph is the amount of pigmentation in the scar at the month denoted in the X-axis. In this particular graph, the P value is less than 0.05. Overall, this graph shows that the improvements in pigmentation of the scar for those patients who used the Composition greatly increased over the 3-month period as compared to those patients who used the silicone cream.

Figure 8:
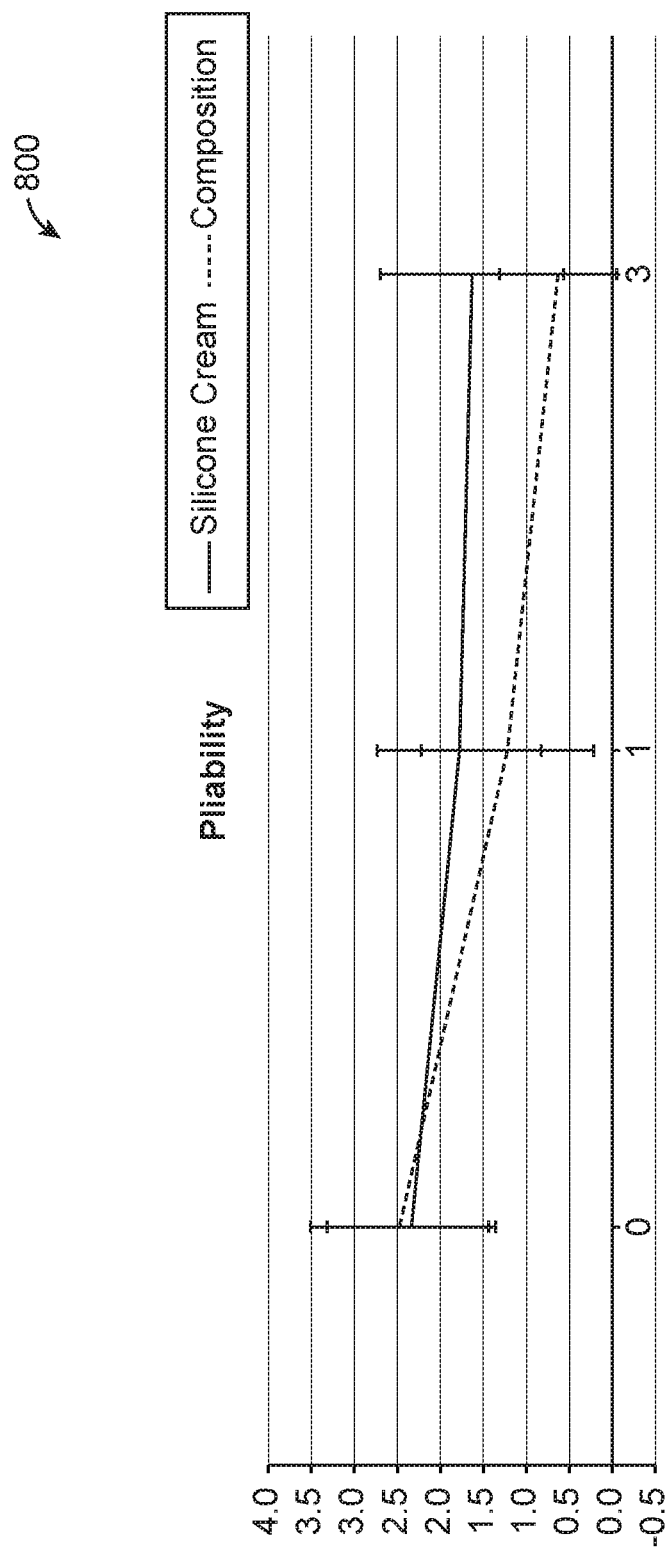
FIG. 8 is a graph showing the improvement in the pliability of the scar in those patients using the composition in an embodiment of the present composition.

Referring now to FIG. 8, a graph showing the improvements in pliability of the scar over the course of the study for each of the creams tested is shown at 800. The dashed line shows the results for the Composition, whereas the solid line shows the results for the silicone cream. Located along the X-axis of this graph is the month in which the reading was taken (e.g., 0=start of study, 1=$1^{st}$ month after beginning usage, 3=$3^{rd}$ month after beginning usage). Located along the Y-axis of this graph is the amount of pliability in the scar at the month denoted in the X-axis. In this particular graph, the P value is less than 0.05. Overall, this graph shows that the improvements in pliability of the scar for those patients who used the Composition greatly increased over the 3-month period as compared to those patients who used the silicone cream.

Figure 9:
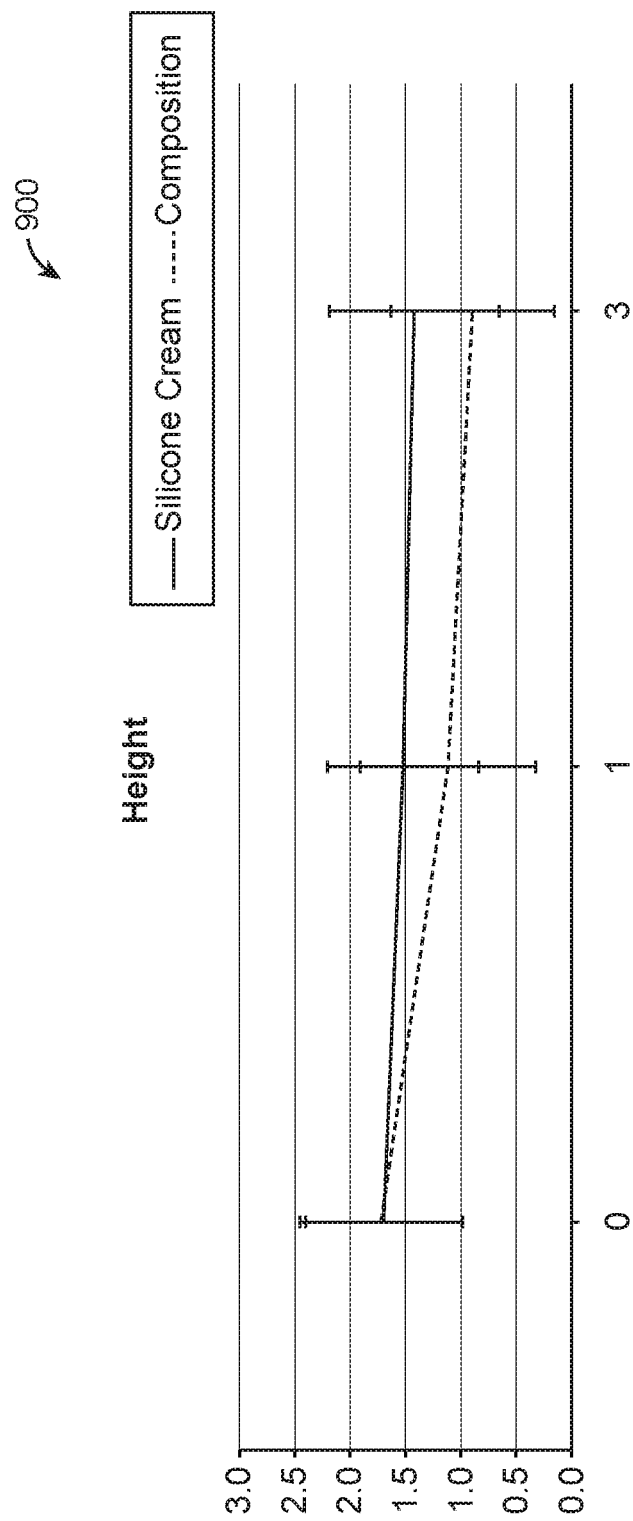
FIG. 9 is a graph showing the improvement in the height of the scar in those patients using the composition in an embodiment of the present composition.

Referring now to FIG. 9, a graph showing the improvements in the height of the scar over the course of the study for each of the creams tested is shown at 900. The dashed line shows the results for the Composition, whereas the solid line shows the results for the silicone cream. Located along the X-axis of this graph is the month in which the reading was taken (e.g., 0=start of study, 1=$1^{st}$ month after beginning usage, 3=$3^{rd}$ month after beginning usage). Located along the Y-axis of this graph is the height of the scar at the month denoted in the X-axis. In this particular graph, the P value is less than 0.05. Overall, this graph shows that the improvements in the height of the scar for those patients who used the Composition greatly increased over the 3-month period as compared to those patients who used the silicone cream.

Figure 10:
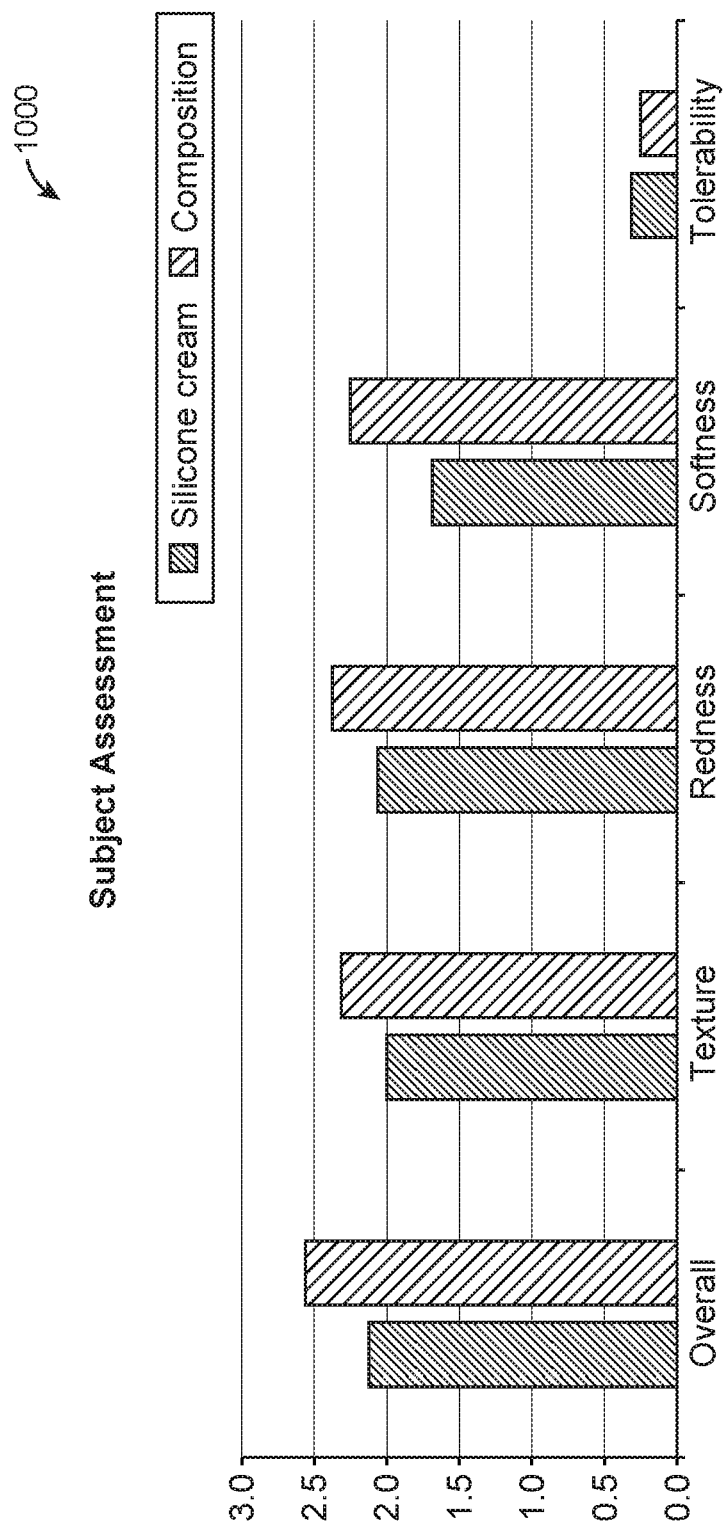
FIG. 10 is a graph showing the results of a subjective assessment conducted regarding the appearance of the scars on the patients using the composition in an embodiment of the present composition.

Referring now to FIG. 10, a graph showing the results of a subjective assessment conducted regarding the appearance of the scars on the patients for each of the creams tested is shown at 1000. Composition, whereas the blue bar shows the results for the silicone cream. Located along the X-axis of this graph is the specific subjective trait evaluated (e.g., texture, redness, softness, tolerability and the overall appearance). Located along the Y-axis of this graph is the assessment score. In this particular table, the P value is less than 0.05. Overall, the graph shows that subject appearance of the scar was found to be better among those who used the Composition.

General Procedures

The ingredients in the Composition and methods of this composition are either known compounds or are compounds that can be prepared from readily available starting. While optimum reaction conditions may vary with the particular reactants or solvent used, but such conditions can be determined by one skilled in the art by routine optimization procedures.

Topical cosmetic forms and topical pharmaceutical dosing forms can include creams, gels, ointments, lotions, pastes and the like. Lotions typically comprise oil-in-water emulsions using a substance such as cetearyl alcohol to keep the emulsion together. The key components are the aqueous and oily phases, an emulgent to prevent separation of these two phases, and the composition of the present composition. A wide variety of other ingredients such as fragrances, glycerol, petroleum jelly, dyes, preservatives and stabilizing agents may be added as well, along with polymers such as polyethylene glycol, thickeners, solids and the like. Liquid or solid formulations may include enhanced delivery technologies such as liposomes, microsomes and the like.

Liquid forms, such as lotions suitable for topical administration as in "drops" may include a suitable aqueous or non-aqueous vehicle with buffers, suspending and dispensing agents, penetration enhancers, and the like.

The above-described components for liquid, semisolid and solid topical compositions are merely representative, and other known topicals may be employed with the present composition.

The following formulation examples illustrate representative pharmaceutical compositions of this composition. The present composition, however, is not limited to the following pharmaceutical compositions.

General Active Formula

A compound having the ingredients listed above is prepared and may be ground to a fine power or suspended in a media.

EXAMPLE 3

At room temperature, in the amounts listed in Table 1, add water, aloe barbadensis leaf juice, glycerin, water and *Centella Asiatica* Extract mixture together and mix until all solids are dissolved. Add sodium hyaluronate and continue mixing until the mixture is fully hydrated. Add Hydroxyethyl Acrylate/Sodium Acryloyldimethyl Taurate Copolymer and glycerin and mix until homogenous. Add TGF B3, IL-10, bFGF, and mix until homogeneous. Add Dimethicone, Ethoxydiglycol, PPG-12 SMDI Copolymer, Phenoxyethanol and Ethylhexylglycerin, Etrahexyldecyl Ascorbate, and Cyclopentasiloxane & Dimethicone Crosspolymer and mix until homogenous.

In the method of the composition, the composition is administered topically. The method includes the step of topically applying a composition, which includes a therapeutically effective amount of active composition for the treatment of scar tissue, as defined above, and a pharmaceutically acceptable topical carrier, to existing scar tissue. In the method, an effective amount of the topical composition of the composition may be applied to the skin as needed.

More preferably, the topical composition of the present composition is applied to the skin at least once a day beginning after the formation of scar tissue, and preferably at least three times (e.g., morning, noon and bedtime) in a 24-hour period.

A topical formulation of the composition preferably includes a pharmaceutically acceptable topical carrier. Many pharmaceutically acceptable topical carriers are known to those skilled in the art. The compounds in the composition may be dissolved, dispersed and/or suspended in the topical carrier.

Exemplary topical carriers may include creams, ointments, lotions, pastes, jellies, sprays, aerosols, topical pharmaceutical carriers, which accomplish direct contact between the active ingredients of the topical composition of the present composition and the pore of the skin. One type of pharmaceutically acceptable carrier is a hydrophilic ointment base. Suitable hydrophilic ointment bases are known to persons skilled in the art.

While the present composition has been described in connection with what are presently considered to be the most practical and preferred embodiments, it is to be understood that the present composition is not limited to these herein disclosed embodiments. Rather, the present composition is intended to cover all of the various modifications and equivalent arrangements included within the spirit and scope of the appended claims.

Although specific features of various embodiments of the composition nvention may be shown in some drawings and not in others, this is for convenience only. In accordance with the principles of the composition, the feature(s) of one drawing may be combined with any or all of the features in any of the other drawings. The words "including", "comprising", "having", and "with" as used herein are to be interpreted broadly and comprehensively and are not limited to any physical interconnection. Moreover, any embodiments disclosed herein are not to be interpreted as the only possible embodiments. Rather, modifications and other embodiments are intended to be included within the scope of the appended claims.

I claim:

1. A composition for treating cutaneous condition which comprises 0.200 wt. % *Aloe Barbadensis* Leaf Juice, 10.000 wt. % Cyclopentasiloxane and Dimethicone Crosspolymer, 6.000 wt. % Dimethicone, 2.000 wt. % Ethoxydiglycol, 2.000 wt. % Glycerin, Water and *Centella Asiatica* Extract Mixture, 18.000 wt. % Glycerin, 3.000 wt. % Hydroxyethyl Acetate/Sodium Acryloyldimethy Taurate Copolymer, 1.100 wt. % Phenoxyyethanol and Ethylexylglycerin, 2.00 wt. % PPG-12 SMDI Copolymer, 0.004 wt. % GMP Grade Recombinant Human TGF-B3, 0.075 wt. % GMP Grade Recombinant Human IL10, 0.250 wt. % GMP Grade Recombinant Human bFGF, 0.500 wt. % Sodium Hyaluronate, 2.000 wt. % Tetrahexyldecyl Ascorbate, 53 wt % Water.

2. A composition for treating cutaneous condition which consists of 0.200 wt. % *Aloe Barbadensis* Leaf Juice, 10.000 wt. % Cyclopentasiloxane and Dimethicone Crosspolymer, 6.000 wt. % Dimethicone, 2.000 wt. % Ethoxydiglycol, 2.000 wt. % Glycerin, Water and *Centella Asiatica* Extract Mixture, 18.000 wt. % Glycerin, 3.000 wt. % Hydroxyethyl Acetate/Sodium Acryloyldimethy Taurate Copolymer, 1.100 wt. % Phenoxyyethanol and Ethylexylglycerin, 2.00 wt. % PPG-12 SMDI Copolymer, 0.004 wt. % GMP Grade Recombinant Human TGF-B3, 0.075 wt. % GMP Grade Recombinant Human IL10, 0.250 wt. % GMP Grade Recombinant Human bFGF, 0.500 wt. % Sodium Hyaluronate, 2.000 wt. % Tetrahexyldecyl Ascorbate, and water to make 100%.

\* \* \* \* \*